United States Patent [19]

Sias et al.

[11] 3,951,854

[45] Apr. 20, 1976

[54] STABILIZED ANALYTICAL STANDARDS

[75] Inventors: Roy C. Sias; William L. Groves, Jr., both of Ponca City, Okla.

[73] Assignee: Continental Oil Company, Ponca City, Okla.

[22] Filed: Oct. 4, 1974

[21] Appl. No.: 512,794

Related U.S. Application Data

[63] Continuation-in-part of Ser. No. 435,354, Jan. 21, 1974, abandoned, Continuation of Ser. No. 262,808, June 14, 1972, abandoned.

[52] U.S. Cl. .............................. 252/408; 23/230 R; 73/61 R; 252/33; 252/33.2; 252/33.4; 356/70; 356/243
[51] Int. Cl.$^2$ ..................... C09K 3/00; C10M 1/40; C10M 3/34; G01N 23/223; G01N 33/22
[58] Field of Search ........... 252/408, 33, 33.2, 33.4; 356/70, 243; 73/61 R; 23/230 R

[56] References Cited
UNITED STATES PATENTS

| | | | |
|---|---|---|---|
| 2,420,068 | 5/1947 | Duncan | 252/47.5 |
| 2,481,585 | 9/1949 | Freeman | 252/33.2 |
| 2,606,872 | 8/1952 | Gasser et al. | 252/33 |
| 2,989,564 | 6/1961 | Ambrose et al. | 260/501 |
| 3,368,971 | 2/1968 | Retzloff et al. | 252/33.4 |
| 3,649,661 | 3/1972 | Otto et al. | 252/33 |
| 3,691,075 | 9/1972 | Sias | 252/33 |
| 3,711,406 | 1/1973 | Lowe | 252/33.4 |
| 3,764,533 | 10/1973 | Hunt et al. | 252/33 |
| 3,773,813 | 11/1973 | Hunt | 252/33 |
| 3,785,976 | 1/1974 | Hunt | 252/33 |

OTHER PUBLICATIONS

"Duomeens," Armour Chemical Division Publication, pp. 1–4, (Feb. 1956).

*Primary Examiner*—Benjamin R. Padgett
*Assistant Examiner*—T. S. Gron
*Attorney, Agent, or Firm*—Cortlan R. Schupbach

[57] ABSTRACT

This invention is directed to stabilization of analytic standards comprising (a) an oil-soluble metal sulfonate wherein said metal is selected from the group consisting of molybdenum, vanadium, iron, boron, beryllium, tin, silver, copper, magnesium, or mixtures thereof, (b) a normally liquid hydrocarbon diluent and (c) a stabilizing amount of an oil-soluble amine compound.

5 Claims, No Drawings

STABILIZED ANALYTICAL STANDARDS

This is a continuation-in-part of application Ser. No. 435,354, filed Jan. 21, 1974, now abandoned, which was a continuation of application Ser. No. 262,808, filed Jun. 14, 1972, now abandoned.

This invention relates to oil-soluble metal sulfonate compositions of improved stability which are useful as analytical standards.

In recent years it has been found that superior analytic standards for spectrographic equipment can be prepared from oil-soluble metal sulfonates and metal dispersions in said sulfonates by dissolving such materials in predetermined quantities in a suitable solvent to provide metal levels as low as 1 ppm. Such standards should have indefinite shelf life and any combination of metals should be capable of being combined without precipitation of the metal constituents.

While the use of oil-soluble metal sulfonates as analytical standards has been established and recognized, problems have been encountered with certain metals such as molybdenum, beryllium, tin, copper, magnesium, vanadium, iron, boron and silver. Such compositions, upon prolonged storage, have suffered from the development of an acidic type odor similar to the odors of $H_2S$, $SO_2$, and HCl. Further, upon prolonged storage, we have found the previous metal sulfonate compositions showed poor blend stability at low metal concentrations and a visual precipitate could be observed, and yet with others where the visual blend stability problem was not shown the problem could be detected by instrumental methods of analysis. Problems have been encountered particularly with the blend stability of these metal sulfonates at low metal concentrations around 100 parts per million and less. Therefore, a need has been recognized for stable oil-soluble metal sulfonate compositions.

Therefore, an object of the present invention is to provide an analytical standard comprising an oil-soluble metal sulfonate composition with improved stability. Another object of the present invention is to provide an economical, dependable and efficient method for preparing such analytical standards from readily available chemical compounds.

Another object of the present invention is to provide for the preparation of analytical standards comprising oil-soluble metal sulfonate compositions of the metals selected from the group molybdenum, vanadium, iron, boron, beryllium, tin, silver, copper, magnesium, or mixtures thereof. These and other objects, advantages and features of the present invention will be apparent to those skilled in the art from a reading of the following detailed description.

In accordance with the invention, it has been discovered that certain oil-soluble amine compounds may be added to oil-soluble metal sulfonates wherein said metal is selected from the group consisting of molybdenum, vanadium, iron, boron, beryllium, tin, silver, copper, magnesium, or mixtures thereof, to achieve an analytical standard which does not suffer from the problems of the prior art; i.e., odor and stability problems.

In general, the improved analytical standards comprise the oil-soluble metal sulfonate, the oil-soluble amine compound and a normally liquid hydrocarbon diluent. The standards may be prepared by admixing the components, together or in any sequence of addition, under agitation for a suitable period of time to insure uniform blending. Heat may be applied during blending to temperatures in the range of 20° to 150°C. After blending, the resulting product may be stripped of any highly volatile materials as desired. In addition, the product may be clarified by filtration through an inert solid such as alumina, diatomaceous earth, pumice and the like.

The oil-soluble metal sulfonates which are stabilized in accordance with the invention are those wherein the metal is selected from the group consisting of molybdenum, vanadium, iron, boron, beryllium, tin, silver, copper, magnesium, or mixtures thereof. In general, this invention provides for stabilization of these metal sulfonates wherein the total content of these metals in the analytical standard is less than about 2000 ppm with any single metal being present in an amount less than about 1000 ppm. It is only with the lower concentrations of these metals that stability problems arise so as to require the use of the invention. Concentrations of these metals higher than the above specified values have essentially no stability problems. The invention is particularly applicable to analytical standards wherein the total content of these metals is less than 100 ppm.

The above mentioned oil-soluble metal sulfonates are well known in the art being described in U.S. Pat. Nos. 3,240,710; U.S. 3,773,813; U.S. 3,785,976; and in Ser. No. 148,264 (now abandoned) and Ser. No. 240,273 (now abandoned). In general, these oil-soluble metal sulfonates are the above mentioned metal salts of oil-soluble hydrocarbon sulfonic acids having an average molecular weight of at least about 400, and preferably in the range of about 450 to 600.

The stabilizing oil-soluble amine compounds include

A. amines defined by

wherein R is a saturated or unsaturated aliphatic hydrocarbon having 6 to 24 carbon atoms; R' is hydrogen or a saturated or unsaturated aliphatic hydrocarbon having 1 to 24 carbon atoms; and R" is hydrogen, a saturated or unsaturated hydrocarbon having 1 to 24 carbon atoms, or -R'''NH$_2$ wherein R''' is a saturated aliphatic hydrocarbon having 2 to 6 carbon atoms;

B. monocarboxylic acid salts of the amines defined in (A) wherein the monocarboxylic acid is a saturated or unsaturated aliphatic hydrocarbon carboxylic acid having 6 to 24 carbon atoms; and C. oil-soluble sulfonic acid salts of the amines defined in (A) wherein the oil-soluble sulfonic acid is a hydrocarbon sulfonic acid having an average molecular weight of at least 400, preferably in the range of 400 to 600.

Especially desirable stabilization results have been obtained wherein the amine compound is the diamine 1,3-diaminopropane having an alkyl moiety selected from the group consisting of n-coco, n-tallow, n-soya and n-oleyl. The compound 1,3-diaminopropane can be represented by the general formula R-NH (C$_3$H$_6$NH$_2$) wherein R is an alkyl group representing the coco, tallow, soya or oleyl moiety. These diamines are available commercially under the tradename DUOMEEN C, T, O and S. A stabilizing amount of the amine compound is employed. While any amount of amine compound will produce some stabilizing effects, it is usually desirable to employ at least about 1 part by weight amine compound per part by weight metal in the metal sulfonate. In general, about 1 to 800 parts by weight amine compound per part by weight metal in the metal sulfonate will be used for most applications.

Expressed in another way, the metal sulfonate and the amine compound can be present in a ratio of about 1/0.3 to about 1/300, respectively, based on the metal content of the metal sulfonate and the amino content of the amine compound. In some applications such ratio may be in the range of 1/0.3 to 1/8.

Any normally liquid hydrocarbon or mixture thereof may be employed as the diluent provided the viscosity of the diluent is not greater than about 600 centistokes at 100°F. Preferably, the viscosity of the diluent is not greater than about 300 centistokes at 100°F.

It is pointed out that the above described stabilized analytical standard may also contain additional oil-soluble metal sulfonates which do not suffer from stability problems as do the above described metal sulfonates. Such oil-soluble metal sulfonates which do not require stabilization include those wherein the metals are calcium, lead, aluminum, lithium, and the like.

In order to more fully illustrate the nature of the present invention, the following experimental data is given. However, it is to be understood that the experimental data is for illustrative purposes only and are not intended to unduly limit or restrict the present invention. In each experiment the metal sulfonate was derived from sulfonic acid from an alkyl aromatic which was predominantly di-n-alkylbenzenes having a molecular weight of about 420, unless otherwise specified.

EXAMPLE I

Two amine sulfonates were prepared from a hydrocarbon sulfonic acid having an average molecular weight of about 508 and N-coco-1,3-diaminopropane as follows:

|  | A | B |
|---|---|---|
| Sulfonic acid[1] (grams) | 200.0 | 200.0 |
| N-coco-1,3-diaminopropane (grams) | 63.9 | 33.5 |
| % excess amine, approx | 100 | 5 |
| 80 Pale Oil diluent (grams) | 32.4 | 32.4 |
| Isopropyl alcohol (ml) | 50 | 50 |

[1]Total acid 1.101 meq/g, sulfonic acid 1.034 meq/g, wt. % nonvolatiles 56.84.

All the reactants, except the oil, were charged to a creased flask, heated to reflux and refluxed for 1 hour. The volatiles were taken overhead to 100°C, oil charged and volatiles removed to 150°C. The reaction mass was stripped with $N_2$ gas for 15 minutes, then filtered through diatomaceous earth. Both products A and B were bright and fluid.

Blends were prepared in isooctane employing products A and B from above and an oil-soluble iron sulfonate prepared from a hydrocarbon sulfonic acid having an average molecular weight of about 500 (as described in application Ser. No. 711,920, filed Mar. 11, 1968, now abandoned) as follows:

|  | C | D |
|---|---|---|
| Fe sulfonate, (g) | 1.0 | 1.0 |
| Product A (g) | 1.5 | — |
| Product B (g) | — | 1.5 |
| Isooctane, (ml) | 250 | 250 |

Each blend, C and D, had about 4800 ppm amine sulfonate and about 100 ppm Fe (by weight). After blending in a pint bottle each blend was shaken by a mechanical shaker for 5 minutes then stored at ambient temperature in natural light. No visual sediment was observed after three weeks storage for blends C and D; whereas a control sample of the same Fe concentration (approximately 100 ppm by weight) showed visual sediment after 10 days under similar conditions.

EXAMPLE II

An analytical standard was prepared by initially forming a solution of isooctane containing about 1000 ppm of the amine sulfonate identified as product A in Example I. This solution was then used to dilute isooctane solutions containing 5000 ppm (weight) Fe and V, respectively, to form analytical standards, one containing 990 ppm (weight) amine sulfonate and 50 ppm (weight) Fe and the other containing 990 ppm (weight) amine sulfonate and 50 ppm (weight) V. Control samples of 50 ppm (weight) Fe and 50 ppm (weight) V were also prepared without any amine compound. The blends were stored at ambient temperature in glass. After one month no visible sediment was observed in the analytical standards of the invention whereas the control samples exhibited visible sediment after two weeks.

EXAMPLE III

Analytical standards were prepared using 1 g. of the iron salt of an oil-soluble hydrocarbon sulfonic acid having an average molecular weight of about 508, 250 ml of isooctane and a specified quantity of one of the following amine compounds
A - N-coco-1,3-diaminopropane mono-salt of an oil-soluble hydrocarbon sulfonic acid having an average molecular weight of about 752. B - N-coco-1,3-diaminopropane di-salt of an oil-soluble hydrocarbon sulfonic acid having an average molecular weight of about 1260. C - N-coco-1,3-diaminopropane (DUOMEEN CD). D - N-tallow-1,3-diaminopropane di-salt of oleic acid. The analytical standards contained 100 ppm Fe by weight.

TABLE A

| Analytical Standard No. | Amine Compound Type | Amine Compound Quantity | Months to Precipitate |
|---|---|---|---|
| 1 | None |  | 1 |
| 2 | B | 1.5g (6900ppm) | 7+* |
| 3 | A | 1.5g (6900ppm) | 7+* |
| 4 | A | 1.5g (6900ppm) | 6+* |
| 5 | C | 1.65g (7550ppm) | 5+* |
| 6 | C | 0.25g (1140ppm) | 5+* |
| 7 | D | 1.65g (8600ppm) | 5+* |
| 8 | D | 0.25g (1300ppm) | 5+* |

*samples had no precipitation after the indicated number of months.

EXAMPLE IV

The experiments of Example III were repeated except that the analytic standards were prepared having 80 ppm V by weight.

TABLE B

| Analytical Standard No. | Amine Compound Type | Amine Compound Quantity | Months to Precipitate |
|---|---|---|---|
| 1 | None | | 3 |
| 2 | A | 1.2g (5500ppm) | 6+[a] |
| 3 | B | 1.2g (5500ppm) | 6+[a] |
| 4 | C | 0.9g (4150ppm) | 0.5 |
| 5 | C | 0.25g (1140ppm) | 6+[a] |
| 6 | D | 1.65g (8600ppm) | 6+[a] |
| 7 | D | 0.25g (1300ppm) | 6+[a] |

[a] samples had no precipitation after the indicated number of months.

EXAMPLE V

Several analytical standards were prepared containing the oil-soluble vanadium salt of a hydrocarbon sulfonic acid having an average molecular weight of about 508 diluted in isooctane to the extent that the vanadium metal content was about 50 ppm (by weight). Several levels of certain stabilizing amine compounds (those of Example III) were added to some of the standards while others were left unstabilized for controls. The standards, in glass flasks, were set in a window and periodically observed for haze or precipitation (kick-out). The details and results of this experiment are indicated in the table.

TABLE C

| Standard No. | Amine Compound Type | Amine Compound Level (ppm, weight) | Time for Haze Or Precipitation |
|---|---|---|---|
| 1 | None | — | 4 days |
| 2 | None | — | 11 days |
| 3 | None | — | 13 days |
| 4 | None | — | 14 days |
| 5 | A | 285 | 16 days |
| 6 | A | 570 | 16 days |
| 7 | A | 1140 | 6 weeks |
| 8 | A | 1140 | 7 weeks |
| 9 | A | 2280 | 3 months |
| 10 | B | 285 | 16 days |
| 11 | B | 570 | 7 days |
| 12 | B | 1140 | 3 weeks |
| 13 | C | 570 | 18 days |
| 14 | C | 1140 | 4 days |
| 15 | C | 2280 | 3 days |
| 16 | D | 1300 | 6 months |

EXAMPLE VI

The experiments of Example V were repeated but using the oil-soluble iron salt of a hydrocarbon sulfonic acid having an average molecular weight of about 508 at a level of 50 ppm (weight) of Fe. The details and results are indicated in the table.

TABLE D

| Standard No. | Amine Compound Type | Amine Compound Level (ppm, weight) | Time for Haze Or Precipitation |
|---|---|---|---|
| 1 | None | — | 17 days |
| 2 | None | — | 6 weeks |
| 3 | None | — | 2 months |
| 4 | C | 570 | 9 months+ |
| 5 | C | 1140 | 9 months+ |
| 6 | A | 1140 | 9 months |
| 7 | D | 1300 | 7 months |

EXAMPLE VII

The experiments of Example V were repeated but using the oil-soluble molybdenum salt of a hydrocarbon sulfonic acid having an average molecular weight of about 508 at a level of 50 ppm (weight) of Mo. The details and results are indicated in the table.

TABLE E

| Standard No. | Amine Compound Type | Amine Compound Level (ppm, weight) | Time for Haze Or Precipitation |
|---|---|---|---|
| 1 | None | — | 11 weeks |
| 2 | A | 1140 | 9 months+ |

EXAMPLE VIII

The experiments of Example V were repeated but using the oil-soluble tin salt of a hydrocarbon sulfonic acid having an average molecular weight of about 508 at a level of 50 ppm (weight) of Sn. The details and results are indicated in the table.

TABLE F

| Standard No. | Amine Compound Type | Amine Compound Level (ppm, weight) | Time for Haze Or Precipitation |
|---|---|---|---|
| 1 | None | — | 5 weeks |
| 2 | None | — | 6 weeks |
| 3 | C | 570 | 3 months |
| 4 | C | 1140 | 10 months+ |
| 5 | B | 1140 | 5 months |
| 6 | A | 1140 | 1 year+ |

EXAMPLE IX

Two analytical standards were prepared, each containing twenty oil-soluble metal sulfonate standards diluted in a hydrocarbon oil having a viscosity of 245 centistokes at 100°F. The oil-soluble metal sulfonates were metal salts of hydrocarbon sulfonic acids having an average molecular weight of 508 wherein the metals were silver, aluminum, boron, barium, beryllium, cadmium, chromium, copper, iron, magnesium, manganese, molybdenum, sodium, nickel, lead, silicon, tin, titanium, vanadium and zinc. The concentration of each metal was 10 ppm by weight. One sample was unstabilized and the other was stabilized with 1940 ppm by weight of amine A (Example III).

The blends were analyzed for molybdenum content by an excited X-ray fluorescence technique. This technique is well known by those skilled in the art. Simply put, the sample is subjected to gamma rays from a radioisotope which causes the emission of X-rays from the metals thereof. The X-ray energy is contained over a period of time at several detection channels at which the energy for the particular metal in question is most concentrated. The sum of the counts for four channels for 4000 seconds is used as a measure for the molybdenum concentration. The results of the analysis were as follows:

TABLE G

| | Stabilized | Unstabilized |
|---|---|---|
| After 4 months | 18,952 | 16,469 |
| After 6 months | 14,906 | 7,812 |

TABLE G-continued

| | Stabilized | Unstabilized |
|---|---|---|
| After 11 months | 9,815 | 4,932 |

The data reveals that the 4 months old unstabilized sample when compared with the 4 months old stabilized blend had approximately a 12 percent lower count showing a greater stability problem. Similar results were obtained after 6 months and 11 months.

Having thus described the invention, we claim:

1. A stabilized analytical standard containing a predetermined total metal content of less than about 2000 ppm by weight with any single metal being present in an amount less than about 1000 ppm by weight which comprises
    a an oil-soluble metal salt of a hydrocarbon sulfonic acid wherein the metal is selected from the group consisting of molybdenum, vanadium, iron, boron, beryllium, tin, silver, copper, magnesium and mixtures thereof,
    b a normally liquid hydrocarbon diluent, and (c) a stabilizing amount of an oil-soluble amine compound selected from
    1. amines defined by

wherein R is a saturated or unsaturated aliphatic hydrocarbon having 6 to 24 carbon atoms; R' is hydrogen or a saturated or unsaturated aliphatic hydrocarbon having 6 to 24 carbon atoms; R' is hydrogen or a saturated or unsaturated aliphatic hydrocarbon having 1 to 24 carbon atoms; and R'' is a saturated aliphatic hydrocarbon having 2 to 6 carbon atoms;
    2. monocarboxylic acid salts of the amines defined in (1) wherein the monocarboxylic acid is a saturated or unsaturated aliphatic hydrocarbon carboxylic acid having 6 to 24 carbon atoms; and
    3. oil-soluble sulfonic acid salts of the amines defined in (1) wherein the oil-soluble sulfonic acid is a hydrocarbon sulfonic acid having an average molecular weight of at least 400, preferably in the range of 400 to 600.

2. A stabilized analytical standard according to claim 1 wherein any single metal is present in an amount less than about 100 ppm by weight.

3. A stabilized analytical standard according to claim 1 wherein the amine compound is employed in an amount of at least 1 part by weight per part by weight metal.

4. A stabilized analytical standard according to claim 3 wherein the amine compound is employed in an amount of 1 to 800 parts by weight per part by weight metal.

5. A stabilized analytical standard according to claim 1 wherein the metal salt and amine compound are present in a ratio of about 1/0.3 to 1/8, respectively, based on the metal content of the metal salt and the amino content of the amine compound.

* * * * *

UNITED STATES PATENT OFFICE
CERTIFICATE OF CORRECTION

PATENT NO. : 3,951,854
DATED : April 20, 1976
INVENTOR(S) : Roy C. Sias and William L. Groves, Jr.

It is certified that error appears in the above-identified patent and that said Letters Patent are hereby corrected as shown below:

Column 7, line 29, the formula should read:

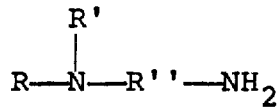

Column 8, line 2, delete "R' is hydrogen or a saturated or unsaturated aliphatic hydrocarbon having 6 to 24 carbon atoms;"

*Signed and Sealed this*

Seventeenth *Day of* August 1976

[SEAL]

*Attest:*

RUTH C. MASON
*Attesting Officer*

C. MARSHALL DANN
*Commissioner of Patents and Trademarks*